US00PP33506P3

(12) United States Plant Patent
Bull

(10) Patent No.: US PP33,506 P3
(45) Date of Patent: Sep. 21, 2021

(54) ***HELIANTHUS* PLANT NAMED 'BULLHELIDEC 0201'**

(50) Latin Name: ***Helianthus decapetalus* hybrid**
Varietal Denomination: BullHelidec 0201

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 17/096,493

(22) Filed: Nov. 12, 2020

(65) Prior Publication Data

US 2021/0144945 A1 May 20, 2021

Related U.S. Application Data

(60) Provisional application No. 62/974,135, filed on Nov. 15, 2019.

(51) Int. Cl.
*A01H 5/02* (2018.01)
*A01H 6/14* (2018.01)
*A01H 5/12* (2018.01)

(52) U.S. Cl.
USPC ..... Plt./436
CPC ..... *A01H 6/14* (2018.05); *A01H 5/02* (2013.01); *A01H 5/12* (2013.01)

(58) Field of Classification Search
USPC ..... Plt./436
CPC ..... A01H 6/14
See application file for complete search history.

*Primary Examiner* — Anne Marie Grunberg
(74) *Attorney, Agent, or Firm* — The Webb Law Firm

(57) ABSTRACT

A new and distinct variety of *Helianthus* plant having a compact growth habit and large, yellow colored blooms.

2 Drawing Sheets

Botanical classification: *Helianthus decapetalus* hybrid.
Varietal denomination: 'BullHelidec 0201'.

BACKGROUND OF THE INVENTION

The present invention comprises a new and distinct variety of *Helianthus* plant, botanically known as *Helianthus decapetalus* hybrid, and having the varietal denomination of 'BullHelidec 0201'. The new variety was developed in August of 2017 in Gönnebek, Germany as a result of a naturally occurring mutation of *Helianthus* variety named 'BullHeli 1216' (unpatented). The purpose of the breeding program was to produce *Helianthus* varieties with improved growth and large flowers. The new variety was first asexually reproduced via in-vitro tissue culture cuttings in Gönnebek, Germany in February of 2018. 'BullHelidec 0201' is more compact, has more flowers, and an earlier flowering time than 'BullHeli 1216'.

When compared to *Helianthus* variety named 'Capenoch Star' (unpatented), the varieties are similar in flower color, but 'BullHelidec 0201' is more compact, more self-branching, has a shorter crop time, smaller leaves, and larger flowers than 'Capenoch Star'. Further, the following characteristics generally distinguish 'BullHelidec 0201' from other *Helianthus* varieties known to the breeder:

Compact growth habit;
Single, large flowers;
Small and attractive foliage;
Improved self-branching;
Desirable hardiness; and
More uniform crop growth.

The new variety has been trial and field tested and has been found to retain its distinctive characteristics and remain true to type through successive propagations. The present invention has not been evaluated under all possible environmental conditions. The phenotype may vary with variations in environment without a change in the genotype of the plant.

BRIEF DESCRIPTION OF THE DRAWINGS

The photographic drawings in the form of color photographs provided herein illustrate the new variety at approximately 17 weeks of age, with the colors being as nearly true as is possible with color illustrations of this type.

DETAILED BOTANICAL DESCRIPTION

Figure 1:
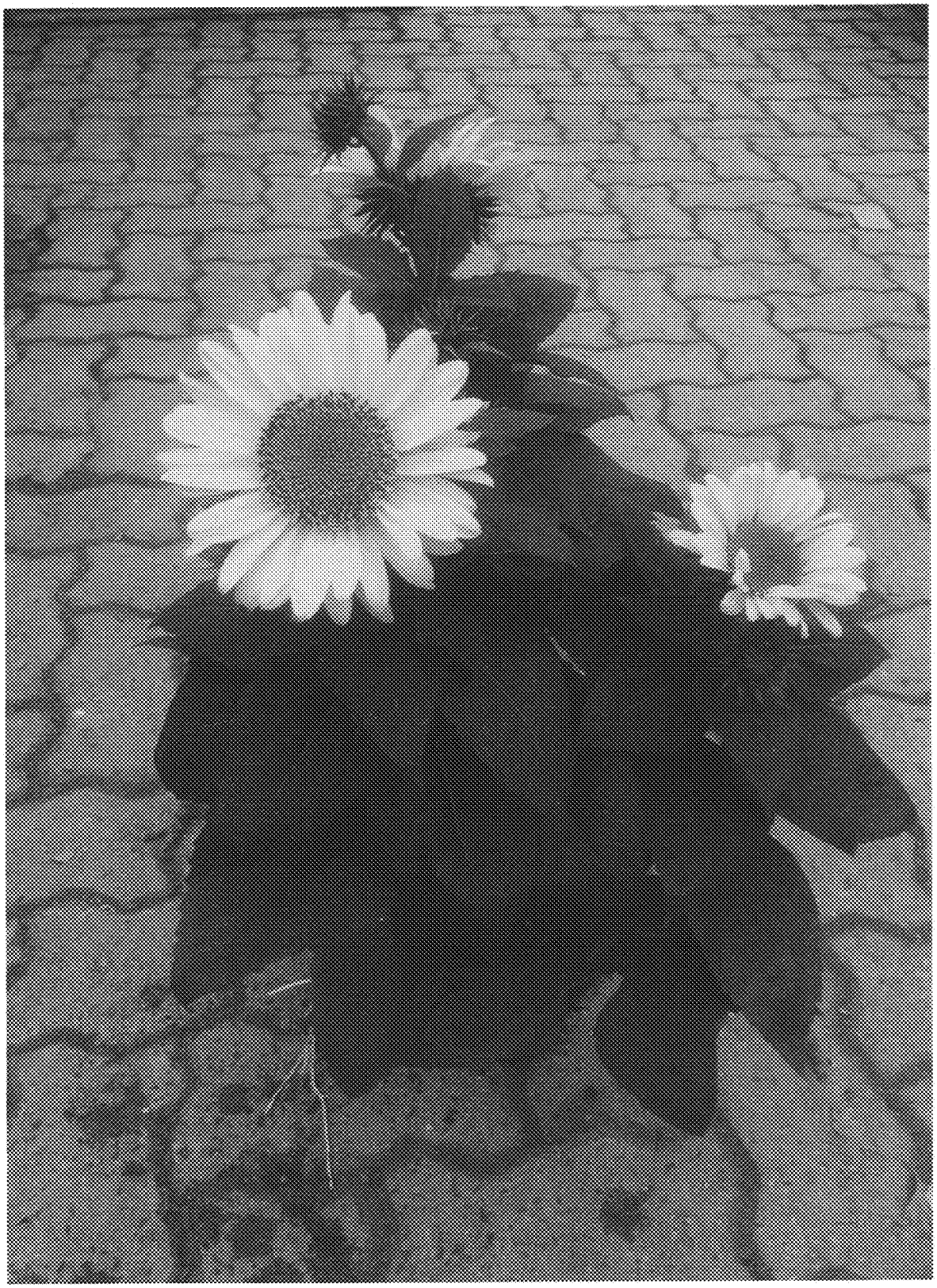
FIG. 1 shows an entire plant of the new variety.
Figure 2:
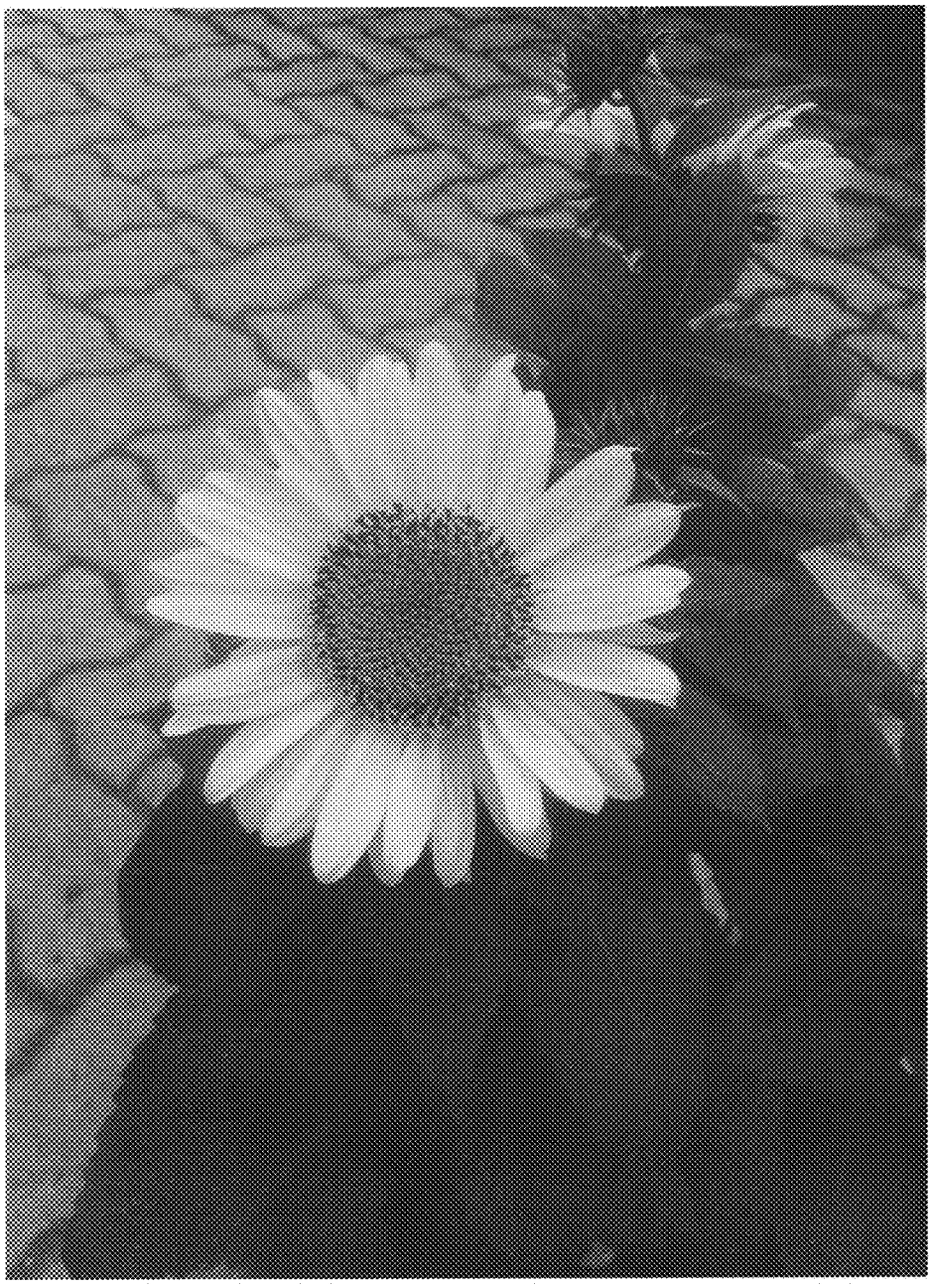
FIG. 2 shows a close-up view of a bloom of the new variety.

The following detailed description sets forth the characteristics of the new variety. The data which defines these characteristics was collected as a result of asexual reproductions via in-vitro tissue culture cuttings in Gönnebek, Germany The new variety was grown outside in 13.0 cm pots under normal field production conditions in Gönnebek, Germany. The color readings were taken outside under natural light and the variety was approximately 17 weeks of age when described. Color references are primarily to The 2015 R.H.S. Colour Chart of The Royal Horticultural Society of London, Sixth Edition, except where terms of ordinary significance are used.

Plant

Time to initiate roots: About 14 days at about 18° C.

*Time to develop roots.*—About 21-28 days at about 18° C.

*Time to produce a finished flowering plant from a rooted cutting.*—About 8-12 weeks in a 13.0 cm container.

*Rooting habit.*—Very freely branching with numerous roots of medium thickness.

*Form.*—Upright.

*Average height.*—Approximately 25.0-50.0 cm.

*Average width.*—Approximately 20.0-30.0 cm.

*Disease/pest resistance.*—None observed to date.

*Temperature tolerance.*—Tolerates temperatures from −15° C. to 35° C.

*Drought tolerance.*—Average, nothing unusual noticed to date.

*Branching habit.*—One dominate branch with a few side branches.

*Lateral branches.*—Number: 3-8 per plant. Length: 20.0-30.0 cm. Diameter: 3.0-12.0 mm.

*Internode length.*—2.0-10.0 cm.

*Angle.*—Upright.

*Strength.*—High.

*Texture.*—Stable and rough.

*Color.*—Yellow-Green Group RHS 144C, with older branches aging to Brown Group RHS 200C.

Foliage:

*Arrangement.*—Alternate or opposite; single sessile.

*Length.*—3.0-20.0 cm.

*Width.*—2.0-12.0 cm.

*Shape of leaf.*—Aristate.

*Apex.*—Acuminate.

*Base.*—Obtuse.

*Margin.*—Serrate.

*Texture* (*both surfaces*).—Rough. Color: Young leaves: Upper surface: Green Group RHS N138B. Lower surface: Green Group RHS N138B. Mature leaves: Upper surface: Green Group RHS NN137B. Lower surface: Green Group RHS 147B.

*Petiole.*—Length: 0.5-7.0 cm. Diameter: Varies from from 0.2-1.0 cm throughout the length. Texture: Rough and stable. Color: Yellow-Green Group RHS 146C.

*Veins.*—Venation type: Palmate. Color Upper surface: Green Group RHS 139C. Lower surface: Yellow-Green Group RHS 145A.

Inflorescence

Flower arrangement: Composite; single.

*Flower shape.*—Elliptic ray florets and tubular disc florets.

*Natural flowering season.*—Plants freely flower from July-September in Gönnebek, Germany—7 to 10 weeks after planting.

*Fragrance.*—Slightly sweet.

*Average number.*—5-20 per plant and 3-10 per branch.

*Buds.*—Length: 2.0-4.0 cm. Diameter: 2.5-5.0 cm. Color: Close to Green Group RHS 137B.

*Inflorescence.*—Diameter: 5.0-12.0 cm. Height (depth): 2.0-5.0 cm. Diameter of disc: 2.5-6.0 cm Receptacle height: 1.0-2.0 cm. Receptacle diameter: 3.0-6.0 cm.

*Ray florets.*—Number per inflorescence: Abundant—from 35-50. Arrangement: In two or three whorls. Length: 2.5-4.5 cm. Width: 0.8-1.2 cm. Shape: Elliptical, linear. Apex: Rounded. Base: Acute. Margin: Entire. Texture: Upper surface: Smooth, soft. Lower surface: Smooth, soft. Color: When opening: Upper surface: Close to Yellow Group RHS 12A. Lower surface: Close to Yellow Group RHS 12B. At maturity: Upper surface: Close to Yellow Group RHS 12A. Lower surface: Close to Yellow Group RHS 12B. Ground color description: Pure yellow. Venation: Appearance: Parallel. Color: Upper surface: Close to Yellow Group RHS 12A. Lower surface: Close to Yellow Group RHS 12B.

*Disc florets.*—Number per inflorescence: Numerous—more than 100. Arrangement: In the center of receptacle. Length: 10.0-20.0 mm. Width: 2.0 mm. Shape: Tubular. Apex: Five-pointed. Color: Immature: Yellow-light brown. At maturity: Yellow with a shine of brown.

*Phyllaries.*—Number per inflorescence: Many—from 50-100. Arrangement: In 5 or 6 whorls. Length: 1.0-2.0 cm. Width: 4.0-5.0 mm. Shape: Acicular. Apex: Pointed, sharp. Base: Fused. Margin: Entire. Texture: Upper surface: Rough, uneven. Lower surface: Rough, uneven. Color: Immature: Upper surface: Close to Green Group 137D. Lower surface: Close to Green Group 137B. At maturity: Upper surface: Close to Green Group 137D. Lower surface: Close to Green Group 137B.

Reproductive organs:

*Androecium.*—Presence: On ray and disc florets. Number (per floret): 2. Filament length: 10.0 mm. Filament color: Light yellow. Anther: Shape: Linear. Length: 5.0 mm. Color: Close to Brown Group RHS 200A. Pollen: Color: Yellow. Amount: Plentiful.

*Gynoecium.*—Presence: Only in disc florets. Pistil length: 12.0-15.0 mm. Stigma: Shape: Two-parted. Color: Close to Yellow Group RHS 15A. Style: Length: 1.0 mm. Color: Close to Yellow Group RHS 15A.

Seeds: None produced.

I claim:

1. A new and distinct variety of *Helianthus* plant named 'BullHelidec 0201', as is herein described and illustrated.

* * * * *